(12) United States Patent
Schumaker et al.

(10) Patent No.: US 7,679,078 B2
(45) Date of Patent: Mar. 16, 2010

(54) BIS-ANTHRACENYL CHIROPTICAL COMPOSITIONS

(75) Inventors: Robert R. Schumaker, San Jose, CA (US); James J. Marek, Jr., Huntsville, AL (US); James Parakka, San Bruno, CA (US)

(73) Assignee: California Molecular Electronics Corporation, Huntsville, AL (US)

( * ) Notice: Subject to any disclaimer, the term of this patent is extended or adjusted under 35 U.S.C. 154(b) by 835 days.

(21) Appl. No.: 11/078,965

(22) Filed: Mar. 10, 2005

(65) Prior Publication Data

US 2006/0202193 A1    Sep. 14, 2006

(51) Int. Cl.
*H01L 29/08*    (2006.01)
*C07D 339/02*    (2006.01)

(52) U.S. Cl. .......................... 257/40; 549/89; 549/510

(58) Field of Classification Search ................... 257/40; 549/89, 510
See application file for complete search history.

(56) References Cited

U.S. PATENT DOCUMENTS

| | | | |
|---|---|---|---|
| 5,237,067 A | 8/1993 | Schumaker | 546/187 |
| 6,124,963 A | 9/2000 | Schumaker | 359/244 |

OTHER PUBLICATIONS

L. Salem, "Narcissistic Reactions: *Synchronism* vs. *Nonsynchronism* in Automerizations and Enantiomerizations", Acc. Of Chem Res., vol. 4, pp. 322-328, (1971).
J.P. Parakka, et al., "Optical Switching In Chiropticenes", Ann. N.Y. Acad. Sci., vol. 1006, pp. 94-103, (2003).
J. March, "Aromaticity", Advanced Organic Chemistry, $3^{rd}$ Ed., John Wiley 7 Sons, Inc., Chapter 2, p. 40, (1985).
H.-Y. Jen, et al., "A New Synthesis of Aromatic Thiols", Tet. Letters, vol. 23, pp. 2001-2004, (1982).
M. Kato, et al., "A Key Intermediate for the Chiral Synthesis of Elemanoids. Synthesis of (+) β-Elemonone", Chem. Letters, pp. 151-154, (1990).
D.-Q. Li, et al., "Chromophoric Self-Assembly Multilayers. Organic Superlattice Approaches to Thin-Film Nonlinear Optical Materials", J.Am. Chem Soc., vol. 112, pp. 7389-7390, (1990).
Aldrich Handbook of Fine Chemicals and Laboratory Equipment for 2003-2004, pp. 1080-1083, (2003).
K. Mislow, "Sterioisomerism", Introduction to Stereochemistry, W.A. Benjamin, Inc., newYork, $2^{nd}$ Ed., Chapter 2, pp. 65-66, (1966).
H. Rau, "Asymmetric Photochemistry in Solution", Chem. Rev., vol. 83, pp. 535-547, (1983).
H. Durr, Perspectives in Phtochromism: A Novel System Based on the 1,5-Electrocyclization of Heteranalogous Pentdienzyl Anions, Angew, Int. Ed. Engl., vol. 28, pp. 413-431, (1989).

*Primary Examiner*—Rebecca L Anderson
*Assistant Examiner*—Joseph R Kosack

(57) ABSTRACT

Optoelectronic materials are provided that are bistable organic tautomeric compositions that intraconvert dithio or diseleno carbamate esters and cyclic 1,3-dithia- or -diselena-2-iminium salts of π-conjugated bis-anthracenyl compounds. Specifically disclosed are compounds having the formula:

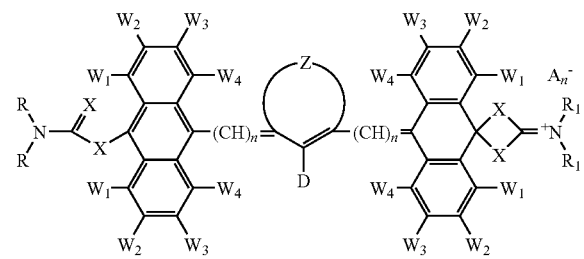

where X is sulfur or selenium; where the R and $R_1$ groups are alkyl or alkyl that together form a ring of carbon atoms; where $A_n$ is the anion of a strong acid; and where the Z element is a chiral ring-completing system of atoms that changes chirality on tautomerization. These molecules are in themselves molecular-sized optoelectronic switching devices.

33 Claims, No Drawings

BIS-ANTHRACENYL CHIROPTICAL COMPOSITIONS

BACKGROUND OF THE INVENTION

1. Field of the Invention

The present invention relates to a class of novel narcissistic valence tautomeric molecules that individually function as optoelectronic switching devices. More specifically, these intramolecular devices are polyene-linked bis-anthracenyl compounds that are optically active and bear a dichalcogenide carbamate ester on one terminal position and a dichalcogenide iminium salt on the other terminal position, to provide compounds that are capable of undergoing valence tautomerization between degenerate cationic tautomeric forms which are enantiomeric to each other. The present invention describes a class of optoelectronic compositions which can be resolved and arranged as molecular switching devices useful for application as chemical sensors or for the transmission, modulation, storage or processing of information.

2. Related Art

Chemical compounds that tautomerize between two degenerate structures are known as narcissistic compounds and their tautomerization a narcissistic reaction [L. Salem, *Acc. Chem. Res.*, Vol. 4, pp. 322-328 (1971).] When such narcissistic compounds are asymmetric, narcissistic reaction results in intraconversion between enantiomeric forms of the molecule. In U.S. Pat. No. 5,237,067 (R. R. Schumaker, Aug. 17, 1993), there is described a particular subset of asymmetric narcissistic compounds useful as molecular switching devices, of Formula (1) below:

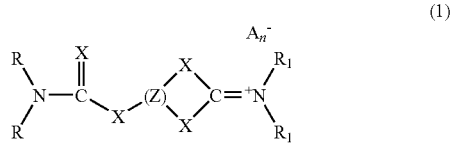

(1)

where X is S or Se; where R and $R_1$ are alkyl, or alkyl that together form a ring of carbon atoms; and where $A_n$ is the anion of a strong acid. The chiral Z element, which changes chirality on tautomerization, is preferably —CH—CH$_2$— so that a preferred structure and its narcissistic reaction is illustrated below (Scheme 1, where R=H):

SCHEME 1

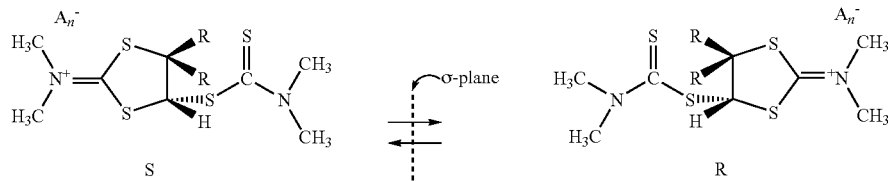

In further elaboration of this structure, a series of derivatives was prepared in which the R substituents were substituted by a variety of multi-cyclic aromatic compounds, for example, 9,9-fluorenyl, 9,9-xanthenyl, 9,9-anthraquinonyl [J. P. Parakka et al., *Ann. N.Y. Acad. Sci.*, Vol. 1006, pp. 94-103 (2003) and references therein]. All of these new narcissistic compounds were shown to be thermally active chiroptical switches. One compound, namely a 9,9-[4,5-bis(dithiophenyl)-anthraquinonyl] derivative, was shown to be optically switchable in the solid state.

Scheme 1 illustrates the principle of coupling together on common atoms, a dithiocarbamate ring-closing and a dithioiminium ring-opening to result in an asymmetric narcissistic reaction.

A non-obvious extension of this principle would be the separation of the coupled ring-closing dithiocarbamate and the ring-opening dithioiminium reaction on two different anthracenyl ring systems that are conjugatively linked by π-bonds that pass through an asymmetric ring system that changes chirality during the narcissistic reaction. This novel design takes advantage of the unique property of the aromatic anthracene molecule to undergo addition across the 9,10 carbons (the central ring) of the molecule [see: J. March, *Advanced Organic Chemistry*, 3$^{rd}$ Edition, John Wiley & Sons, Inc., p. 40 (1985)]. In addition, this novel design permits the incorporation of the asymmetric central ring system of the molecule as a resolved (optically active) component whereas this is not feasible in the structure of Scheme 1.

SUMMARY OF THE DISCLOSURE

In accordance with the present invention, asymmetric narcissistic molecules are provided that comprise polyene-linked bis-anthracenyl compounds that are optically active, have two terminal positions, and bear a dichalcogenide carbamate ester on one terminal position and a dichalcogenide iminium salt on the other terminal position, capable of undergoing valence tautomerization between degenerate cationic forms which are enantiomeric to each other.

Further in accordance with the present invention, a method is provided for forming asymmetric narcissistic molecules comprising conjugated bis-anthracenyl derivatives having the structure:

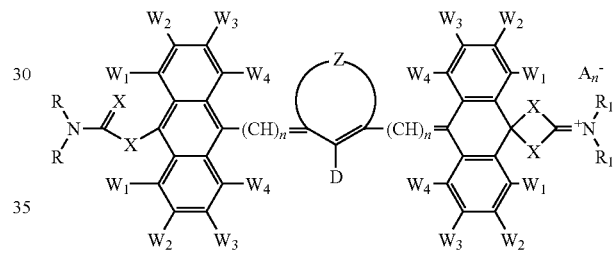

wherein:

$A_n$ is the anion of a strong acid;

X is selected from the group consisting of sulfur, selenium, mixtures thereof, and mixtures of at least two of sulfur, selenium, and oxygen;

the R and $R_1$ groups are selected from the group consisting of alkyls and cycloalkyls and derivatives thereof;

n is 1 or 3;

D is hydrogen or an auxochrome substituted on the molecular chromophore;

$W_1$, $W_2$, $W_3$, and $W_4$ are independently hydrogen or electron-withdrawing substituents; and Z is a chiral ring system of atoms that changes chirality on tautomerization.

The method comprises:

providing an aldehyde;

providing an organo-lithium compound;

reacting together the aldehyde and the organo-lithium compound to form a keto-alcohol, via an organo-metallic aldehyde condensation reaction;

reacting the keto-alcohol with trifloroacetic acid and then a strong acid salt to form the salt of a cyclic iminium ketone;

providing a methylenetriphenylphosphorane; and reacting the cyclic iminium ketone with the methylenetriphenylphosphorane to form the asymmetric narcissistic composition.

Still further in accordance with the present invention, a method is provided for switching asymmetric narcissistic molecules comprising polyene-linked bis-anthracenyl compounds that are optically active, have two terminal positions, and bear a dichalcogenide carbamate ester on one terminal position and a dichalcogenide iminium salt on the other terminal position, capable of undergoing valence tautomerization between degenerate cationic forms that are enantiomeric to each other. The method comprises:

providing the molecules as an optically active form;

acentrically orienting and fixing of one optical form;

incorporating a system for the distortion of molecular energy profiles; and laser irradiating to induce formation of the excited state prochiral photo-intermediate while under the influence of an electric field, in which the polarity of the electric field determines the molecular dipole direction and thus the optical activity of the molecules as they return to the ground state.

Yet further in accordance with the present invention, a molecular optoelectronic switching device is provided, comprising asymmetric narcissistic molecules comprising optically active, polyene-linked bis-anthracenyl molecules coupled with electric field directed tautomerism and a mechanism for detecting specific optical states by their chiroptical effect on polarized light.

With reference to the structure depicted above, the switch-action of this intramolecular device is the ring-opening, ring-closing tautomerism between the 1,3-dichalcogenide-2-iminium cations and dichalcogenide carbamoyl esters that shifts the conjugated π-system and thereby changes the chirality of the optically active central ring system. More specifically, the switching process is activated by stimulation of the molecular chromophore that results in ring-opening of the spiro-cyclic iminium group to afford a symmetric bis-(dichalcogenide-carbamoyl)-anthracenyl intermediate cation. Electric field directed ring closure of one or the other of the dichalcogenide-carbamate moieties completes the narcissistic switching process.

Thus, in accordance with the present invention, a molecular-sized optoelectronic device is provided based on a unique molecular design capable of undergoing an asymmetric narcissistic photoreaction. This molecular-based device is generally useful as a rapid, reversible chiroptical switch with application to the storage, display, and routing of information.

Other objects, features, and advantages of the present invention will become apparent upon consideration of the following detailed description.

DETAILED DESCRIPTION OF THE INVENTION

Synthesis of a Preferred Structure

As indicated above, the asymmetric narcissistic molecules comprise polyene-linked bis-anthracenyl compounds that are optically active, have two terminal positions, and bear a dichalcogenide carbamate ester on one terminal position and a dichalcogenide iminium salt on the other terminal position, capable of undergoing valence tautomerization between degenerate cationic tautomeric forms which are enantiomeric to each other. Such molecules may be employed in molecular-sized optoelectronic devices.

In one embodiment, a class of novel cationic valence tautomeric compounds is provided, having the structure shown in Formula (2):

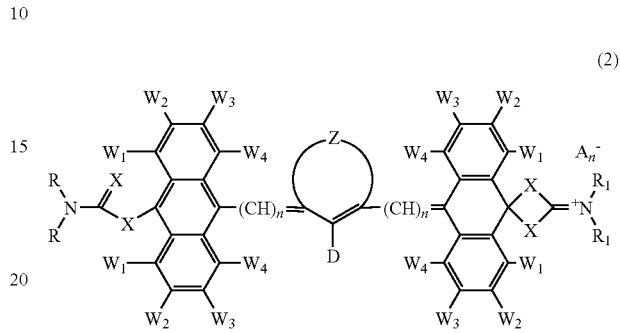

where $A_n$ is the anion of a strong acid; X is sulfur or selenium or mixed sulfur, selenium, or oxygen; the R and $R_1$ groups are alkyl or cycloalkyl and may be variously substituted; n is 1 or 3; D is hydrogen or an auxochrome substituted on the molecular chromophore; $W_1$, $W_2$, $W_3$, and $W_4$ are independently hydrogen or electron-withdrawing substituents; and the Z element is a chiral ring system of atoms which changes chirality on tautomerization.

As noted above, the switch-action of this intramolecular device is the ring-opening, ring-closing tautomerism between the 1,3-dichalcogenide-2-iminium cations and dichalcogenide carbamoyl esters that shifts the conjugated π-system and thereby changes the chirality of the optically active central ring system. More specifically, the switching process is activated by stimulation of the molecular chromophore that results in ring-opening of the spiro-cyclic iminium group to afford a symmetric bis-(dichalcogenide-carbamoyl)-anthracenyl intermediate cation. Electric field directed ring closure of one or the other of the dichalcogenide-carbamate moieties completes the narcissistic switching process.

The possible structures for the central Z portion of the device is governed by the requirement of enantiotropic tautomerism or "psuedoenantiotropic" tautomerism when R≠$R_1$ of Formula (2). On the other hand, in other embodiments, R=$R_1$.

Thus, in accordance with the present invention, a molecular-sized optoelectronic device is provided based on a unique molecular design capable of undergoing an asymmetric narcissistic photoreaction. This molecular-based device is generally useful as a rapid, reversible chiroptical switch with application to the storage, display and routing of information.

Generally in the above Formula (2), X is preferably sulfur, R=$R_1$ and is preferably methyl, $W_1$=$W_2$=$W_3$=$W_4$ and is preferably hydrogen, n=1 and $A_n$ is preferably selected from the group consisting of hexafluorophosphate, tetraphenylborate, trifluoroacetate, and sulfonate. Thus, a preferred structure is illustrated by Formula (3) below. In Formula (3), the components of construction of the molecule, to be described below, are bracketed and labeled (A), (B) and (C).

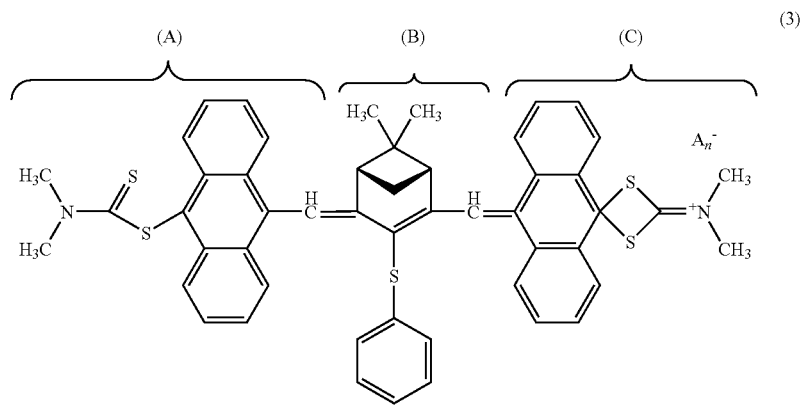

(3)

Broadly, the molecules of the present invention are prepared by a method comprising:
- providing an aldehyde, such as {(1S,5R)-3-thiophenyl-6,6-dimethyl-bicyclo[3.1.1]hep-2-one-3-ene-4-yl}-formaldehyde;
- providing an organo-lithium compound, such as 9-lithio-10-(N,N-dimethyldithiocarbamoyl)-anthracene;
- reacting together the aldehyde and the organo-lithium compounds to form a keto-alcohol, such as 9-{(1S,5R)-3-thiophenyl-66-dimethyl-bicyclo[3.1.1]hep-2-one-3-ene-4-hydroxymethanyl}-10-(N,N-dimethyldithiocarbamoyl)-anthracene via an organo-metallic aldehyde condensation reaction;
- reacting the formed keto-alcohol with trifloroacetic acid and then a strong acid salt to form the salt of a cyclic iminium ketone, such as 9,10-dihydro-9,9-{(1S,5R)-3-thiophenyl-6,6-dimethyl-bicyclo[3.1.1]hep-2-one-3-ene-4-methenyl}-10,10-spiro-(2-dimethyliminium-1,3-dithietanyl)-anthracene anion salt;
- providing a methylenetriphenylphosphorane; such as [10-(N,N-dimethyldithiocarbamoyl)-anthracene-9-yl]-triphenylphosphonium methenide; and
- reacting the cyclic iminium ketone with the methylenetriphenylphosphorane to form the asymmetric narcissistic composition.

To fabricate the preferred structure of Formula (3), reactive intermediates of components (A), (B), and (C) are synthesized for assembly. Reactive component (A) is the anthracene-substituted methylenetriphenylphosphorane illustrated in Formula (4) below.

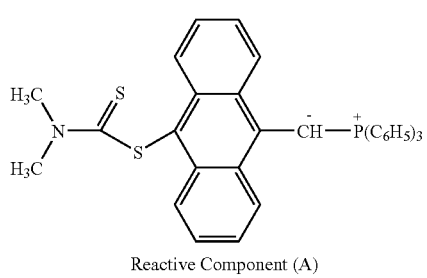

Reactive Component (A)

(4)

Thus, component (A) is attached via the reactive phosphorus ylide, derived by known chemistry from 10-dimethyldithiocarbamato-9-anthraaldehyde which itself is prepared from commercially available 10-chloro-9-anthraaldehyde by reaction with commercial sodium dimethyldithiocarbamate hydrate in dimethylformamide at 80° C.

Component (C) is attached using the reactive anion shown in Formula (5) derived from the known 9-dimethyldithiocarbamoyl-10-bromoanthracene [H.-Y. Jen et al., *Tetrahedron Letters*, Vol. 23, pp. 2001-2004 (1982)] by treatment with butyllithium in tetrahydofuran at −80° C.

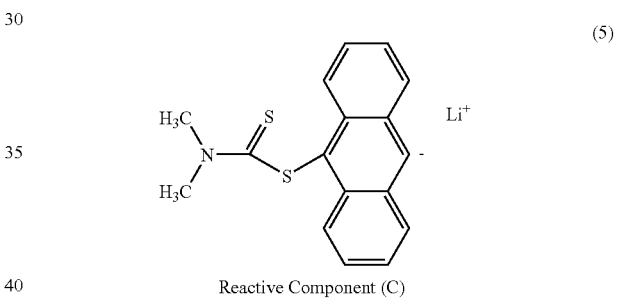

Reactive Component (C)

(5)

The reactive central component (B) is {(1S,5R)-3-thiophenyl-6,6-dimethyl-bicyclo[3.1.1]hep-2-one-3-ene-4-yl}-formaldehyde, illustrated in Formula (6) below. It is readily prepared from commercially available (1S)-(−)-verbenone by oxidation of the allylic methyl group with selenium dioxide and addition of the thiophenyl auxochrome by literature methods [M. Kato et al., *Chemistry Letters*, pp. 151-154 (1990)].

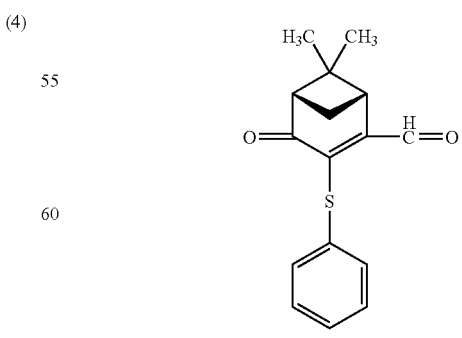

Reactive Component (B)

(6)

Fabrication of the preferred chiroptical switch of Formula (3) is carried out by reaction of the reactive component (C) with the formyl group of component (B) at −80° C. as shown in Scheme 2 below. The resulting intermediate alcohol (D) on treatment with trifluoroacetic acid followed by addition of an anion salt, affords the keto dithioiminium salt (E). Reaction of the keto group of (E) with the reactive component (A) completes the elaboration of the preferred compound of Formula (3).

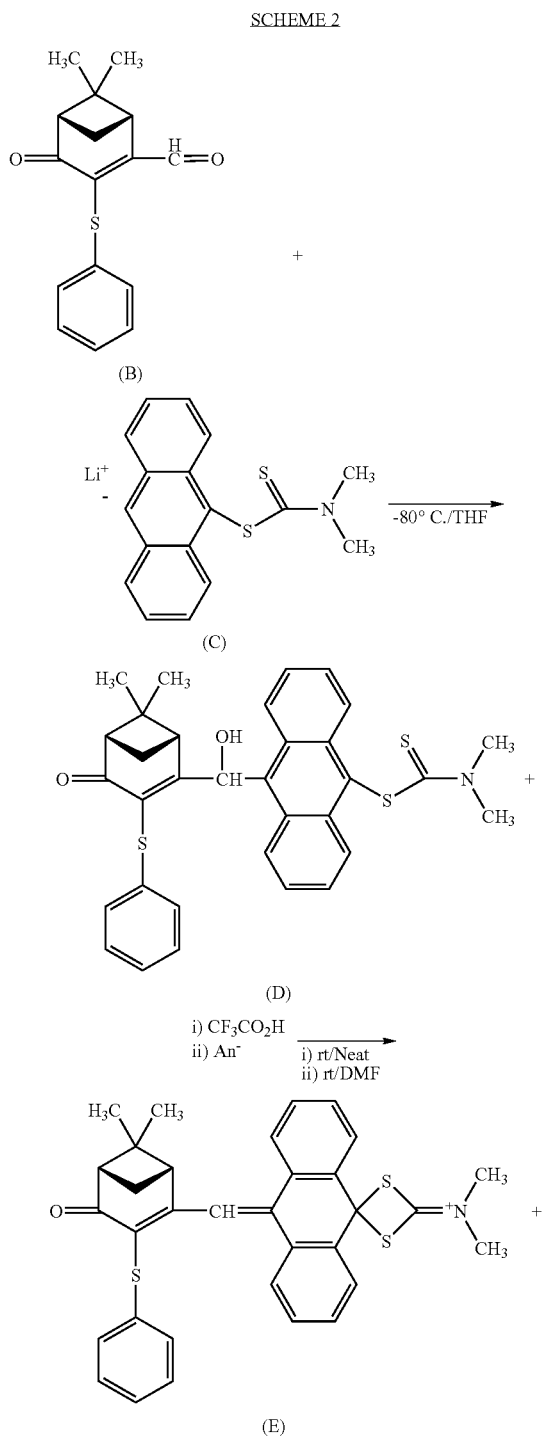

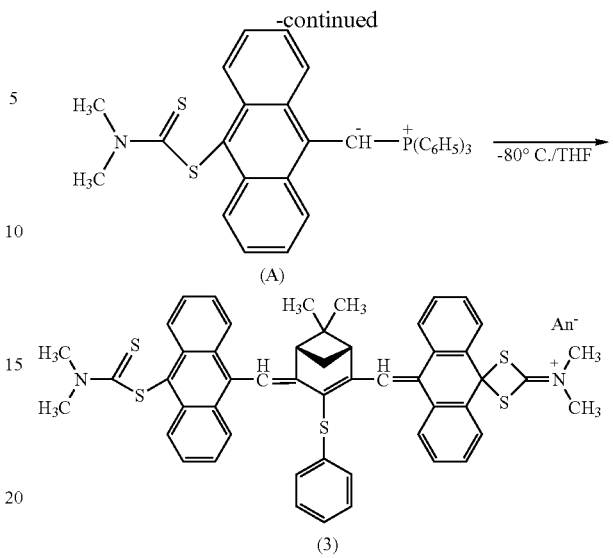

2. Mechanism of the Bis-anthracenyl Chiroptical Switch

The mechanism of the chiroptical switch is depicted in Scheme 3 below for a specific structure that, for illustrative purposes, is attached to electrodes. On activation of the molecular chromophore with light (hv), either chiral form (1 $\underline{S}$, 5$\underline{R}$ or 1$\underline{R}$, 5$\underline{S}$) is converted by ring opening into the identical intermediate prochiral state. The plane of symmetry of this state is the mirror plane of a narcissistic photoreaction. This symmetry plane also bisects the transition state of a thermal synchronous narcissistic reaction that is inoperative because the ground-state activation barrier is too high ($E_{act.}$>25 kcal/mole). The chirogenic reaction centers of the prochiral intermediate state are the two sulfur atoms of the terminal thiocarbonyl groups that constitute the tips of two opposing thiocarbamate dipoles (3.1 Debye). Either dipole can be controlled to ring close preferentially by a directional electric field (E).

To function properly, one chiral form of the asymmetric narcissistic switch molecule must be oriented and fixed on a substrate to differentiate the enantiomers by the direction of the ground state molecular dipole. In the example of Scheme 3, below, the oriented molecule is shown bonded to gold electrodes via sulfur atoms located on the end of the connecting substituents on nitrogen. Subsequent electric field-induced ring closure of the prochiral photointermediate provides optical resolution without evoking absolute asymmetric induction.

3. Molecular Optoelectronic Switching Device

Site selective irradiation of an array of optically active molecules of this invention coupled with electric field-directed tautomerism and the detection of specific optical states by their rotatory effect on polarized light constitutes a molecular-optoelectronic switching device. The functioning of the molecular device involves the following protocol:

(a) The preparation or resolution of the present compounds as optically active forms.

(b) Acentric orientation and fixation of one optical form. This step is used to align and maintain both the molecular dipole moment and optical axis of one enantiomeric form with respect to an external reference system. It may be accomplished by a variety of techniques in various media, including Langmuir-Blodgett films, self assembled covalent attachment and poled polymers, which are well known to one skilled in the art [D.-Q. Li et al., *J. Am. Chem. Soc.*, Vol. 112, pp. 7389-7390 (1990)].

(c) Incorporation of a system for the distortion of molecular energy profiles by, for example, sandwiching the oriented and fixed molecules between two electrodes in a capacitor-type configuration.

(d) Laser irradiation to induce formation of the excited state prochiral photo-intermediate while under the influence of an electric field. The polarity of the electric field determines the molecular dipole direction and thus the optical activity of the molecules as they return to the ground state.

(e) Incorporation of a system for measurement of the chiroptical property of interest. For example, the reflection or transmission of polarized light from the molecules can be analyzed by a system of polarizers and photocells to measure the sign and degree of rotatory effects for the determination of optical activity. For enhanced detection advantage can be taken of the high rotational strengths of inherently dissymmetric chromophores.

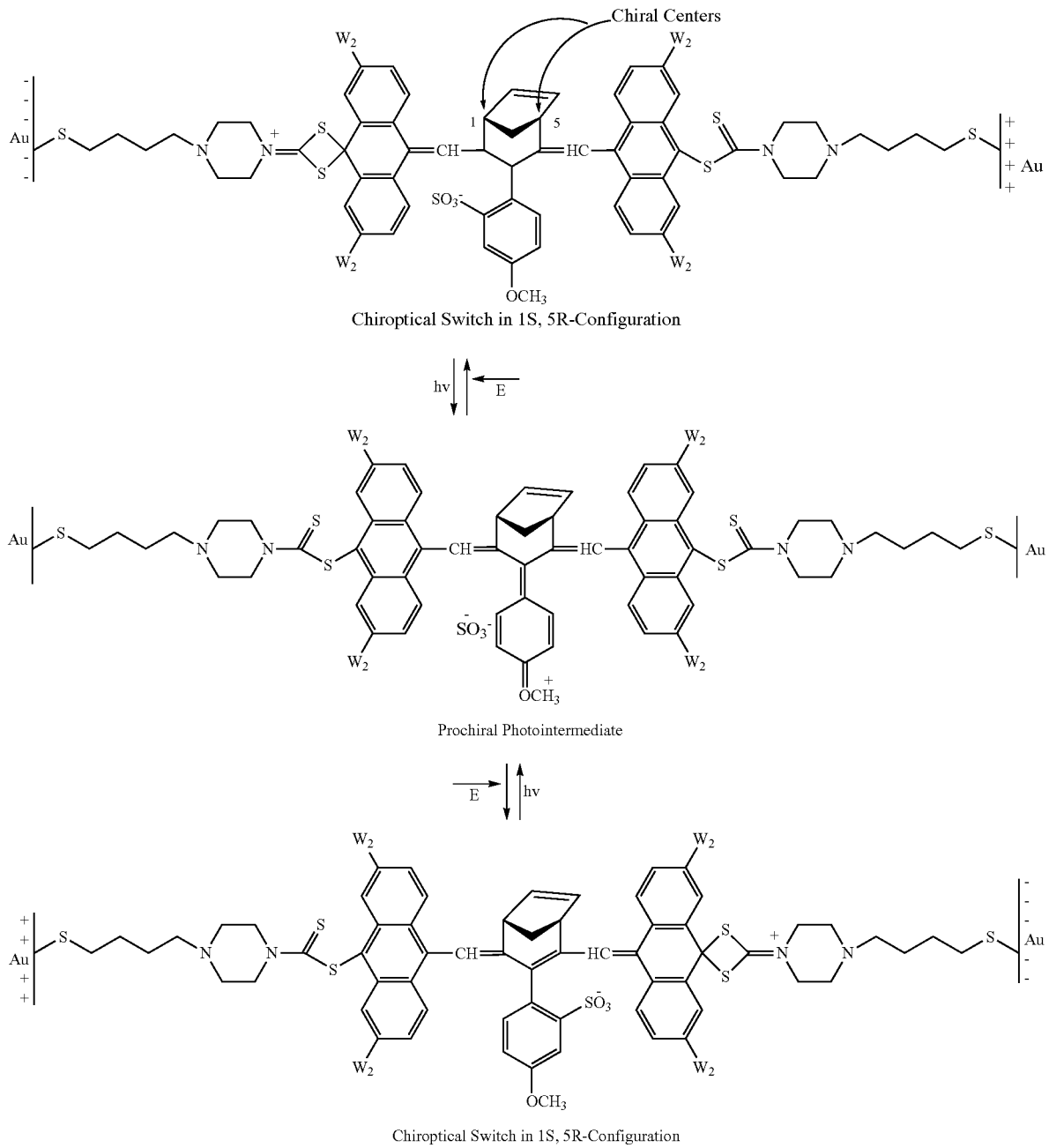

In the functioning of the present molecules as optoelectronic devices, the controlled intraconversion of the oriented and fixed tautomers [steps (a) and (b)] by the imposition of a potential energy distortion [step (c)] combined with laser stimulation [step (d)] constitutes a switching device that is detected by the sign of the rotatory effect of the respective tautomers on the plane of polarized light [step (e)]. In practice, a substrate such as a polymer film is prepared according to step (b) by fixing molecules of this invention thereon. The substrate is then incorporated as the above-described device.

4. Structural Substitutions

For a molecular-based device, structural substitutions are often necessary to fine tune critical properties such as thermal stability, photo stability, sensitivity, reversibility, operating wavelength, and quantum yields. [H. Durr, *Angew. Chem., Int. Ed. Engl.*, Vol. 28, pp. 413-431 (1989)]. In Formula (2), variability in the structure of the bis-anthracenyl switch is indicated by the non-specific substituents labeled: W, D, Z, n, R, $A_n$, and X. Substitutions do not affect the inventive mechanism of the switch but can affect parameters that may need adjustment for proper functioning in much the same way as the accurate working of a pocket watch may be determined by fine adjustment of screws or weights. The range and some effects of these various substitutions are as follows:

W: The W substituents ($W_1$, $W_2$, $W_3$, $W_4$) on the periphery of the two anthracene ring systems are either hydrogen atoms or electron-withdrawing elements such as fluorine or chlorine atoms or the nitro, carboxylate or cyano groups. The number, nature, and position of electron-withdrawing substituents affect the energy requirement for stabilizing positive charge in the anthracenyl ring systems. Thus, their principle effect is to increase the height of the ground-state activation barrier ($E_{act}$) and thereby afford a method to control thermal switching. If these electron-withdrawing substituents are in the $W_2$ or $W_4$ positions [see Formula (2)], then on the spiro-cyclic iminium end of the molecule they become conjugated to the electron-donating auxochrome D. This results in a red shift in the absorption spectra, which lowers the required energy of excitation (hv).

D: The D substituent is located on the central Z ring structure where it is bonded to the middle carbon of the conjugated π-system that joins the anthracenyl rings. The D substituents function as auxochromes on the chromophore that, on excitation, supply the excited-state energy that opens the spiro-cyclic dichalcogenide-iminium ring system; non-limiting examples are selected from the group consisting of —Cl, -phenyl, —O-phenyl, —S-phenyl, and -phenyl-OCH$_3$. It is worth noting that the chemical literature contains numerous examples of cyanine dyes that have similar conjugated systems with centralized auxochromes [see Formula (7) below]. Some of these cyanine dyes are sold as "IR laser dyes" and are listed in the *Aldrich Handbook of Fine Chemicals and Laboratory Equipment for* 2003-2004, on pages 1080-1083. As an example of the expected effect of the various D substitutions, it is observed that changing the auxochrome of Formula (7) below from —S-phenyl to —O-phenyl results in a hypsochromic shift of 24 mμ in $\lambda_{max}$. The central polyene ring systems of the Aldrich Laser Dyes are light stable and synthetically available. Unfortunately, none of these dye systems are optically active, a key requirement for the ring-completing Z component.

(7)

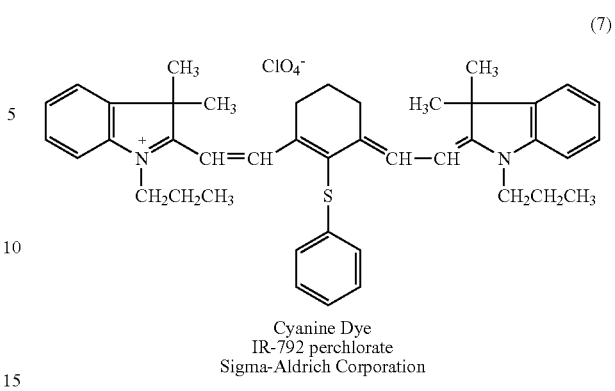

Cyanine Dye
IR-792 perchlorate
Sigma-Aldrich Corporation

Z: The Z substituent is the ring-completing group of atoms that is optically active and switches chirality on tautomerization. Additional criteria for the design of the Z ring system is that it should maximize the measured chiroptical effect, that it be stable to the wavelengths of light it is exposed to (e.g., for reading and writing), and that it be stable to the strong acids used to prepare the spiro-cyclic iminium ring. It is highly advantageous if the Z ring system can be incorporated as a pure enantiomer. In preferred Formula (3), above, we selected a ring system (B) derived from the monoterpene (1S)-(−)-verbenone. This monoterpene is optically active, $[\alpha]^{25}$ −130° (c=10, $C_2H_5OH$), and commercially available starting material. On the other hand, the modified ring system of verbenone may not have the required stability to light and strong acids. In Scheme 3, the central ring is derived from a bicyclo[3.2.1]octadiene derivative. A preferred Z ring moiety possesses an inherently dissymmetric chromophore exhibiting a molecular rotational strength of about 100,000° [see: K. Mislow, *Introduction to Stereochemistry*, W. A. Benjamin, Inc., New York, pp. 65-66 (1965)].

n: The numbers n of the —(CH$_2$)$_n$— vinylene groups in Formula 2 are, for practicable purposes, restricted to 1 and 3 when the central ring system contributes one internal double bond. In these two cases, there are three (see Formula 3) and five conjugated double bond between the anthracenyl moieties, which provide a central polyene carbon atom that can bear a D substituent conjugated to the spiro-cyclic iminium ring. The possibility exists for the formation of geometric isomers associated with the vinylene units, but the same cis/trans mixture will exist for the antipodal form of the molecule. The number n may affect steric interactions between components.

R: The R substituents (R, $R_1$) on nitrogen are alkyl or cyclic alkyl groups that may be variously substituted. They are selected according to the method chosen for alignment and fixation of the switch molecule. R and $R_1$ may be the same (preferred) or different. When R≠$R_1$, the switch becomes pseudo-enantiotropic and will exhibit a small scalemic preference on equilibration. Illustrations of R substituents are the methyl groups of preferred Formula 3 above, whereas in Scheme 3 above, these are replaced by n-butyl-piperazine groups that terminate with sulfur atoms bonded to gold electrodes. A further example is the mixed, R=methyl and $R_1$=n-octane chain, useful for forming Langmuir-Blodgett type supramolecular structures [see: R. R. Schumaker, U.S. Pat. No. 6,124,963, (Sep. 26, 2000)].

$A_n$: The $A_n$ or counter ion to the iminium cation is a strong acid anion, preferably trifluoroacetate, tetraphenylborate, hexafluorophosphate, or sulfonate. As illustrated in Scheme 3, the sulfonate anion may be covalently bonded to the D substituent to form an internal salt (zwitterion).

If a racemic mixture of the chiroptical switch is prepared, it may be resolved via diasteriomeric salt formation with an optically active anion.

X: The X substituents are chalcogenide atoms, preferably sulfur or selenium, although mixed systems containing various combinations of sulfur, selenium, and oxygen are possible. The primary effect of these substitutions will be on the rates of opening and closing the iminium ring system.

The invention now being fully described, it will be apparent to one of ordinary skill in the art that many changes and modification can be made without departing from the spirit and scope of the invention.

What is claimed is:

1. Asymmetric narcissistic molecules comprising polyene-linked bis-anthracenyl compounds that are optically active, have two terminal positions, and bear a dichalcogenide carbamate ester on one terminal position and a dichalcogenide iminium salt on the other terminal position, capable of undergoing valence tautomerization between degenerate cationic forms that are enantiomeric to each other, wherein the asymmetric narcissistic molecules comprise conjugated bis-anthracenyl derivatives having the structure:

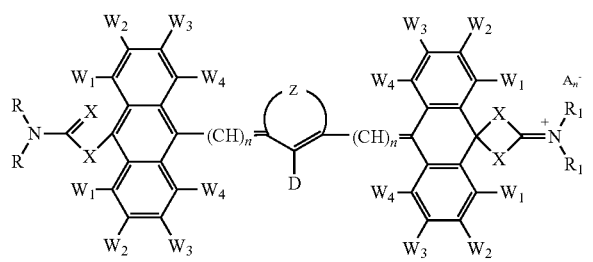

wherein:
$A_n$ is the anion of a strong acid;
X is independently selected from the group consisting of sulfur, selenium, and oxygen;
the R and $R_1$ groups are independently selected from the group consisting of alkyls and cycloalkyls and derivatives thereof;
n is 1;
D is hydrogen or an auxochrome substituted on the molecular chromophore;
$W_1$, $W_2$, $W_3$, and $W_4$ are independently hydrogen or electron-withdrawing substituents; and
Z is a six-membered chiral ring system of atoms that changes chirality on tautomerization.

2. The asymmetric narcissistic compositions of claim 1 wherein $A_n$ is selected from the group consisting of trifluoroacetate, tetraphenylborate, hexafluorophosphate, and sulfonate.

3. The asymmetric narcissistic compositions of claim 1 wherein each X is sulfur or each X is selenium.

4. The asymmetric narcissistic compositions of claim 1 wherein $R_1$ and R are the same.

5. The asymmetric narcissistic compositions of claim 1 wherein the auxochrome is selected from the group consisting of —Cl, -phenyl, —O-phenyl, —S-phenyl, and -phenyl-$OCH_3$.

6. The asymmetric narcissistic compositions of claim 1 wherein Z is selected from the group consisting of (1) a monoterpene (1S)-(−)-verbenone derivative and (2) a bicyclo[3.2.1]octadiene derivative.

7. The asymmetric narcissistic compositions of claim 1 wherein X is sulfur, R is methyl, $W_1=W_2=W_3=W_4$=hydrogen, n=1, and $A_n$ is selected from the group consisting of hexafluorophosphate, tetraphenylborate, trifluoroacetate, and sulfonate, the composition having the structure

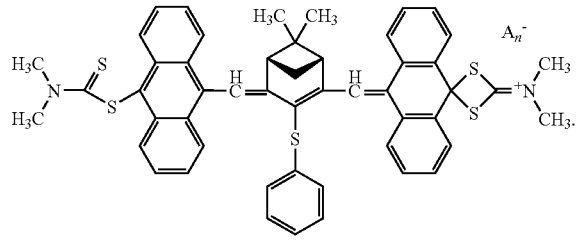

8. A method of forming asymmetric narcissistic molecules that comprise polyene-linked bis-anthracenyl compounds that are optically active, have two terminal positions, and bear a dichalcogenide carbamate ester on one terminal position and a dichalcogenide iminium salt on the other terminal position, capable of undergoing valence tautomerization between degenerate cationic forms that are enantiomeric to each other, wherein the asymmetric narcissistic molecules comprise conjugated bis-anthracenyl derivatives having the structure:

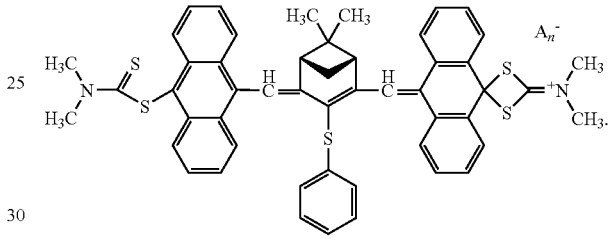

wherein:
$A_n$ is the anion of a strong acid;
X is independently selected from the group consisting of sulfur, selenium, and oxygen;
the R and $R_1$ groups are selected from the group consisting of alkyls and cycloalkyls and derivatives thereof;
n is 1;
D is hydrogen or an auxochrome substituted on the molecular chromophore;
$W_1$, $W_2$, $W_3$, and $W_4$ are independently hydrogen or electron-withdrawing substituents; and
Z is a six-membered chiral ring system of atoms that changes chirality on tautomerization,
the method comprising:
providing an aldehyde;
providing an organo-lithium compound;
reacting together the aldehyde and the organo-lithium compounds to form a keto-alcohol via an organo-metallic aldehyde condensation reaction;
reacting the keto-alcohol with trifluoroacetic acid and then a strong acid anion to form the anion salt of a cyclic iminium ketone;
providing a methylenetriphenylphosphorane; and
by reacting the cyclic iminium ketone with the methylenetriphenylphosphorane to form the asymmetric narcissistic composition.

9. The method of claim 8 wherein $A_n$ is selected from the group consisting of trifluoroacetate, tetraphenylborate, hexafluorophosphate, and sulfonate.

10. The method of claim 8 wherein each X is sulfur or each X is selenium.

11. The method of claim 8 wherein $R_1$ and R are the same.

12. The method of claim 8 wherein $R_1$ is different than R.

13. The method of claim 8 wherein the auxochrome is selected from the group consisting of —Cl, -phenyl, —O-phenyl, —S-phenyl, and -phenyl-$OCH_3$.

14. The method of claim 8 wherein the auxochrome is phenyl substituted in the ortho, meta, or para position by a sulfonate An to form an internal salt.

15. The method of claim 8 wherein the electron-withdrawing substituents are selected from the group consisting of fluorine, chlorine, nitro, carboxylate, and cyano.

16. The method of claim 8 wherein Z is selected from the group consisting of (1) a monoterpene (1S)-(−)-verbenone derivative and (2) a bicyclo[3.2.1]octadiene derivative.

17. The method of claim 8 wherein X is sulfur, R is methyl, $W_1=W_2=W_3=W_4$=hydrogen, n=1, and $A_n$ is selected from the group consisting of hexafluorophosphate, tetraphenylborate, trifluoroacetate, and sulfonate, the composition having the structure

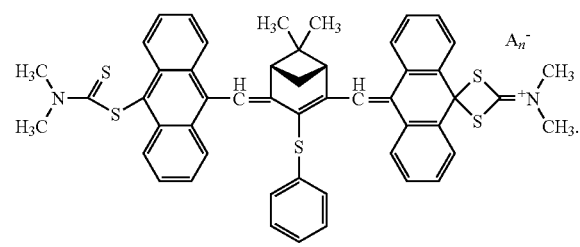

18. The method of claim 17 wherein the method comprises the following reaction scheme:

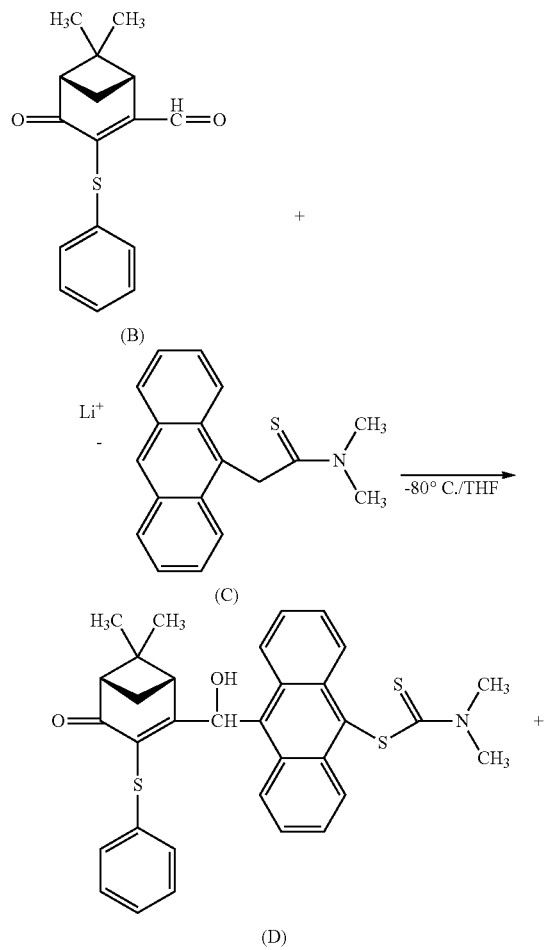

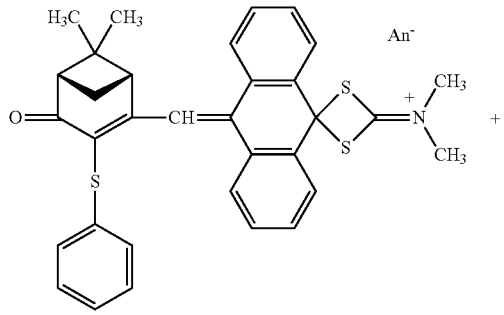

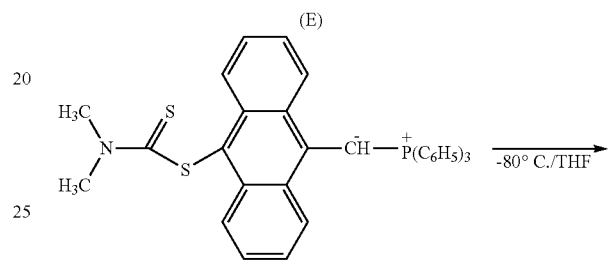

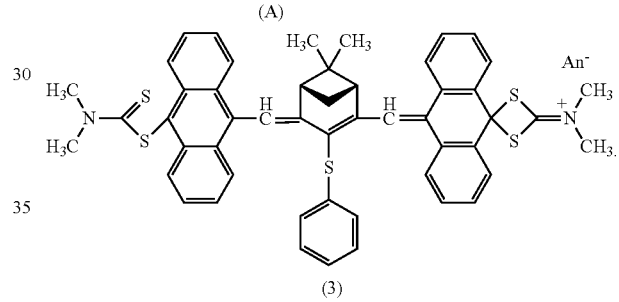

19. The method of claim 8 wherein the method comprises:
providing as the aldehyde {(1S,5R)-3-thiophenyl-6,8-dimethyl-bicyclo[3.1.1]hep-2-one-3-ene-4-yl}-formaldehyde;
providing as the organo-lithium compound 9-lithio-10-(N, N-dimethyldithiocarbamoyl)-anthracene;
reacting together the aldehyde and the organo-lithium compounds to form the keto-alcohol 9-{(1S,5R)-3-thiophenyl-66-dimethyl-bicyclo[3.1.1]hep-2-one-3-ene-4-hydroxymethanyl}-10-(N,N-dimethyldithiocarbamoyl)-anthracene via the organo-metallic aldehyde condensation reaction;
reacting the formed keto-alcohol with trifluoroacetic acid and then a strong acid salt to form the salt of the cyclic iminium ketone 9,10-dihydro-9,9-{(1S,5R)-3-thiophenyl-6,6-dimethyl-bicyclo[3.1.1]hep-2-one-3-ene-4-methenyl}-10,10-spiro-(2-di-methyliminium-1,3-dithietanyl)-anthracene anion salt;
providing as the methylenetriphenylphosphorane [10-(N, N-dimethyldithio-carbamoyl)-anthracene-9-yl]-triphenylphosphonium methenide; and
reacting the cyclic iminium ketone with the methylenetriphenylphosphorane to form the asymmetric narcissistic composition.

20. A molecular optoelectronic switching device comprising asymmetric narcissistic molecules comprising optically active, polyene-linked bis-anthracenyl molecules coupled with electric field directed tautomerism and a mechanism for detecting specific optical states by their chiroptical effect on polarized light, wherein the asymmetric narcissistic molecules have two terminal positions and bear a dichalcogenide carbamate ester on one terminal position and a dichalcogenide iminium salt on the other terminal position, capable of undergoing valence tautomerization between degenerate cationic forms that are enantiomeric to each other, wherein the asymmetric narcissistic molecules comprise conjugated bis-anthracenyl derivative molecules having the structure:

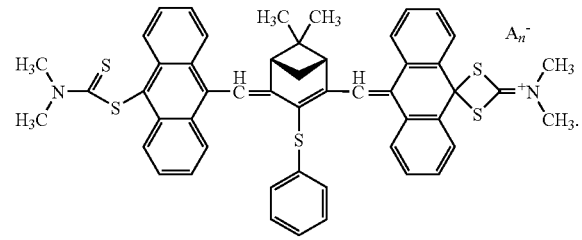

wherein:
$A_n$ is the anion of a strong acid;
X is independently selected from the group consisting of sulfur, selenium, and oxygen;
the R and $R_1$ groups are selected from the group consisting of alkyls and cycloalkyls and derivatives thereof;
n is 1;
D is hydrogen or an auxochrome substituted on the molecular chromophore;
$W_1$, $W_2$, $W_3$, and $W_4$ are independently hydrogen or electron-withdrawing substituents; and
Z is a six-membered chiral ring system of atoms that changes chirality on tautomerization,
the molecule having a molecular dipole moment and an optical axis.

21. The molecular optoelectronic switching device of claim 20 wherein said optically active molecules are sandwiched between two opposed electrodes, to which an electric field may be applied.

22. The molecular optoelectronic switching device of claim 20 further comprising a system for measurement of a chiroptical property of interest.

23. The molecular optoelectronic switching device of claim 22 wherein the system comprises one or more polarizers and one or more photocells to measure the sign and degree of rotatory effects for the determination of optical activity by analyzing the reflection or transmission of polarized light from the molecules.

24. The molecular optoelectronic switching device of claim 20 wherein $A_n$ is selected from the group consisting of trifluoroacetate, tetraphenylborate, hexafluorophosphate, and sulfonate.

25. The molecular optoelectronic switching device of claim 20 wherein each X is sulfur or each X is selenium.

26. The molecular optoelectronic switching device of claim 20 wherein $R_1$ and R are the same.

27. The molecular optoelectronic switching device of claim 20 wherein the auxochrome is selected from the group consisting of —Cl, -phenyl, —O-phenyl, —S-phenyl, and -phenyl-$OCH_3$.

28. The molecular optoelectronic switching device of claim 20 wherein Z is selected from the group consisting of (1) a monoterpene (1S)-(−)-verbenone derivative and (2) a bicyclo[3.2.1]octadiene derivative.

29. The molecular optoelectronic switching device of claim 20 wherein X is sulfur, R is methyl, W is hydrogen, n is 1 and $A_n$ is selected from the group consisting of hexafluorophosphate, tetraphenylborate, trifluoroacetate, and sulfonate, the composition having the structure

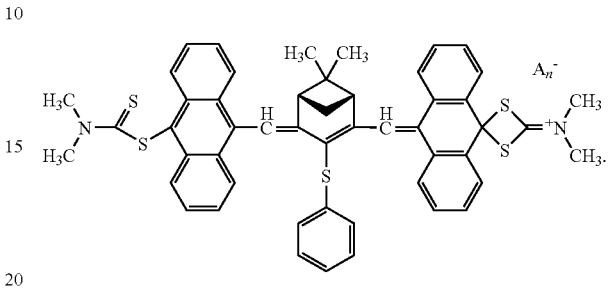

30. The molecular optoelectronic switching device of claim 20 wherein switching involves controlled intraconversion of oriented and fixed tautomers by the imposition of a potential energy distortion combined with laser stimulation that is detected by the sign of the rotatory effect of the respective tautomers on the plane of polarized light.

31. The molecular optoelectronic switching device of claim 30 wherein the molecules are fixed on a substrate which is then incorporated in the switching device.

32. The asymmetric narcissistic molecules of claim 1 a comprising polyene-linked bis-anthracenyl compounds that are optically active, the polyene linkage including a central, six-membered chiral ring system of atoms that changes chirality on tautomerization, the molecules having two terminal positions and bearing a dichalcogenide carbamate ester on one terminal position and a dichalcogenide iminium salt on the other terminal position, the molecules having a conjugated π-system and capable of undergoing valence tautomerization between degenerate cationic forms that are enantiomeric to each other via a ring-opening, ring-closing tautomerism between 1,3-dichalcogenide-2-iminium cations and dichalcogenide carbamoyl esters that shifts the conjugated π-system and thereby changes chirality of the central ring system.

33. The molecular optoelectronic switching device of claim 20 comprising polyene-linked bis-anthracenyl compounds that are optically active, the polyene linkage including a central, six-membered chiral ring system of atoms that changes chirality on tautomerization, the molecules having two terminal positions and bearing a dichalcogenide carbamate ester on one terminal position and a dichalcogenide iminium salt on the other terminal position, the molecules having a conjugated π-system and capable of undergoing valence tautomerization between degenerate cationic forms that are enantiomeric to each other via a ring-opening, ring-closing tautomerism between 1,3-dichalcogenide-2-iminium cations and dichalcogenide carbamoyl esters that shifts the conjugated π-system and thereby changes chirality of the central ring system.

* * * * *